United States Patent [19]

Schacht et al.

[11] 4,136,200

[45] Jan. 23, 1979

[54] PHENYLBUTANOL DERIVATIVES, PROCESSES FOR THEIR PREPARATION AND COMPOSITIONS CONTAINING THEM

[75] Inventors: Erich Schacht; Werner Mehrhof; Albrecht Wild; Joachim Gante; Hans-Adolf Kurmeier, all of Darmstadt, Fed. Rep. of Germany

[73] Assignee: Merck Patent Gesellschaft mit beschränkter Haftung, Darmstadt, Fed. Rep. of Germany

[21] Appl. No.: 810,712

[22] Filed: Jun. 28, 1977

Related U.S. Application Data

[62] Division of Ser. No. 552,959, Feb. 25, 1975, Pat. No. 4,049,823.

[30] Foreign Application Priority Data

| Mar. 1, 1974 [DE] | Fed. Rep. of Germany | 2409761 |
| Jun. 14, 1974 [DE] | Fed. Rep. of Germany | 2428686 |
| Jul. 3, 1974 [DE] | Fed. Rep. of Germany | 2431951 |
| Jul. 26, 1974 [DE] | Fed. Rep. of Germany | 2436012 |

[51] Int. Cl.$^2$ ............................................. C07C 43/20
[52] U.S. Cl. ............................. 424/341; 560/255; 568/637
[58] Field of Search ............... 560/60, 188, 255; 260/618 R, 618 D, 635 R, 520 R, 613 R; 424/341

[56] References Cited

U.S. PATENT DOCUMENTS

| 3,462,483 | 8/1969 | Petrow et al. | 260/618 R |
| 3,859,256 | 1/1975 | Teufel et al. | 260/618 H |

*Primary Examiner*—Bernard Helfin
*Assistant Examiner*—Leah Hendriksen
*Attorney, Agent, or Firm*—Millen & White

[57] ABSTRACT

Phenylbutanol derivatives of the formula Z—C(CH$_3$)(OH)—CH$_2$—Y wherein A is 4-biphenyl or 4-phenoxyphenyl wherein the phenoxy group is unsubstituted or substituted by F, Cl or Br and Y is COOR$^2$ or CH$_2$OR$^3$ where R$^2$ is H or alkyl of 1 to 6 carbon atoms and R$^3$ is H or alkanoyl of 1 to 6 carbon atoms, and their physiologically acceptable salts, possess anti-inflammatory activity and are produced by (a) treating with a solvolyzing agent a compound of the formula Z—C(CH$_3$)(OH)—CH$_2$—W or Z—CX(CH$_3$)—CH$_2$—Y wherein W is a functionally modified carboxy or methylol group different from Y and X is Cl, Br or I or a functionally modified hydroxyl group; or (b) reducing a compound otherwise corresponding to a desired final product but having instead of one of the hydrogen atoms a group which can be reduced or replaced by a hydrogen atom; or (c) oxidizing a compound otherwise corresponding to a desired final product but lacking the tertiary hydroxyl group; or (d) converting a compound otherwise corresponding to a desired final product wherein Z is a 4-phenoxyphenyl group but having instead a 4-OH-, Cl-, Br- or 1-substituted phenyl group into a desired final product; or (e) diazotizing a compound otherwise corresponding to a desired final product wherein Z is a halogen-substituted 4-phenoxyphenyl group but having an —NH$_2$-substituted phenoxy group and reacting the resulting diazonium salt with a halogenating agent.

7 Claims, No Drawings

PHENYLBUTANOL DERIVATIVES, PROCESSES FOR THEIR PREPARATION AND COMPOSITIONS CONTAINING THEM

This is a division, or application Ser. No. 552,959 filed Feb. 25, 1975 now U.S. Pat. No. 4,049,823.

BACKGROUND OF THE INVENTION

This invention relates to novel phenylbutanol derivatives, to processes for their preparation, and to compositions containing them.

Compounds structurally similar to some of the compounds of this invention are described in German DOS No. 2,162,038.

SUMMARY OF THE INVENTION

In a composition aspect, this invention relates to novel phenylbutanol derivatives of Formula I:

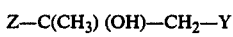
$Z-C(CH_3)(OH)-CH_2-Y$   I wherein Z is 4-biphenylyl or a 4-phenoxyphenyl group of the formula

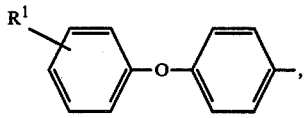

and Y is $COOR^2$ or $CH_2OR^3$, $R^1$ being H, F, Cl or Br, $R^2$ being H or A, $R^3$ being H or alkanoyl having 1 to 6 carbon atoms, and A being alkyl having 1 to 6 carbon atoms, and their physiologically acceptable salts with bases when Y is COOH.

In another composition aspect, this invention relates to pharmaceutical compositions comprising a compound of Formula I.

In process aspects, this invention relates to processes for the preparation of compounds of Formula I and to their use in the treatment of inflammatory conditions.

DETAILED DISCUSSION

In Formula I, $R^1$ is preferably H, F or Cl and preferably is in the m-position or, more preferably, in the p-position, but can also be in the o-position. $R^2$ is preferably H, methyl or ethyl, and $R^3$ is preferably H or acetyl but can also be alkanoyl of any other fatty acid having 1 to 6 carbon atoms, for example, formyl, propionyl, butyryl, isobutyryl, valeryl, isovaleryl, methylethylacetyl, trimethylacetyl, caproyl, isocaproyl and tert.-butylacetyl. When $R^2$ is alkyl, it preferably is methyl or ethyl and secondarily n-propyl, isopropyl, n-butyl, isobutyl, n-pentyl or n-hexyl, but can also be, for example, sec.-butyl, tert.-butyl, isopentyl, neopentyl or isohexyl.

Preferred compounds of this invention are those of Formula I in which at least one of $R^1$, $R^2$ and $R^3$ has one of the preferred values given above, e.g., (a) the 4-biphenyl compounds of Formula I wherein:
 (i) Y is COOH and physiologically acceptable salts thereof with bases, e.g., metals, preferably alkali metals, e.g., Na and K;
 (ii) Y is $COOCH_3$ or $COOC_2H_5$;
 (iii) Y is $CH_2OH$;
 (iv) Y is $CH_2OOCCH_3$;
(b) the 4-phenoxyphenyl compounds of Formula I wherein:
 (i) $R^1$ is H and Y is COOH and physiologically acceptable salts thereof with bases, e.g., metals, preferably alkali metals, e.g., Na and K;
 (ii) $R^1$ is F, Cl or Br and Y is COOH and physiologically acceptable salts thereof with bases, e.g., metals, preferably alkali metals, e.g., Na and K;
 (iii) $R^1$ is H and Y is $COOCH_3$ or $COOC_2H_5$;
 (iv) $R^1$ is F, Cl or Br and Y is $COOCH_3$ or $COOC_2H_5$;
 (v) $R^1$ is H and Y is $CH_2OH$;
 (vi) $R^1$ is F, Cl or Br and Y is $CH_2OH$;
 (vii) $R^1$ is H and Y is $CH_2OOCCH_3$;
 (viii) $R^1$ is F, Cl or Br and Y is $CH_2OOCCH_3$.

In a process aspect, this invention relates to processes for the preparation of a compound of Formula I, which comprises:
 (i) treating a compound of Formula II:

$Z-Q$   II wherein Q is $-C(CH_3)(OH)-CH_2-W$ or $-CX(CH_3)-CH_2-Y$, W is a functionally modified $-COOH$ or $-CH_2OH$ group different from Y, X is Hal or a functionally modified hydroxyl group, Hal is Cl, Br or I, and Y and Z have the values given above, with a solvolyzing agent; or
 (ii) reducing a compound otherwise corresponding to a compound of Formula I but which contains, additionally or instead of an H atom, at least one group which can be reduced or can be replaced by a hydrogen atom; or
 (iii) oxidizing a compound of Formula III:

$Z-CH(CH_3)-CH_2-Y$   III wherein Y and Z have the values given above;
 (iv) reacting a compound of Formula IV:

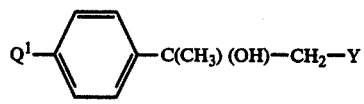

or a salt thereof, with a compound of Formula V:

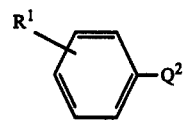

or a salt thereof, wherein one of $Q^1$ and $Q^2$ is OH and the other is X, and $R^1$, X, Y and Z have the values given above; or
 (v) diazotizing a compound of Formula VI:

$Ar-C(OH)(CH_3)-CH_2-Y$   VI wherein Ar is

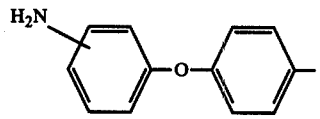

and Y has the values given above, and reacting the resulting diazonium salt with a halogenating agent.

A compound of Formula I obtained by any of the foregoing processes can, if desired, be treated with a reducing, oxidizing, solvolyzing, esterifying or transesterifying agent to convert its Y group into another Y group and/or, when $R^1$ = H in such compound, be treated with a chlorinating or brominating agent to obtain a compound of Formula I wherein $R^1$ is Cl or Br and/or, when Y is a carboxyl group, be treated with a base to convert it into a physiologically acceptable salt thereof.

The processes described above represent particular applications of standard methods described in the literature (for example, in standard works such as Houben-Weyl, Methoden der organischen Chemie ("Methods of Organic Chemistry"), Georg Thieme Verlag, Stuttgart; Organic Reactions, John Wiley & Sons Inc., New York). The reaction conditions which are known and suitable for the respective reactions can be used.

The starting materials for the preparation of the compounds of Formula I can, if desired, be formed in situ in such a way that they are not isolated from the reaction mixture, but are immediately reacted further to give a compound of Formula I. The starting materials for the preparation of the compounds of Formula I are, in general, also new. They can, however, be readily obtained by methods which are in themselves known.

The compounds of Formula I can be obtained, in particular, by solvolysis (preferably hydrolysis) of corresponding functionally modified compounds of Formula II. Solvolysis of the latter compounds may be carried out in an acidic, neutral or alkaline medium at a temperature of from −20° to 300° C.

Hydrochloric acid, sulfuric acid or acetic acid are preferably used to effect acidic solvolysis, while sodium hydroxide, potassium hydroxide, calcium hydroxide, sodium carbonate or potassium carbonate are preferably used for basis solvolysis. The solvent used is preferably water, a lower alcohol, such as methanol or ethanol, an ether, such as tetrahydrofuran (THF) or dioxane, an amide, such as dimethylformamide (DMF), a nitrile, such as acetonitrile, a sulfone, such as tetramethylenesulfone, or a mixture of two or more of these solvents, particularly mixtures containing water.

The solvolysis of an alcohol derivative of the formula Z—CX(CH$_3$)—CH$_2$—Y wherein X is preferably a functionally modified OH group, or Cl, Br or I, is preferred. The OH group can, for example, be functionally modified in the form of one of its alcoholates, preferably one of its zinc alcoholates of the formula Z—C(CH$_3$) (OZnBr)—CH$_2$—Y, such as are formed as primary products in zinc organic syntheses, particularly the Reformatsky reaction, and also in the form of one of its magnesium alcoholates or lithium alcoholates, such as are formed as reaction products in Grignard reactions or reactions with organolithium compounds, in the form of an ester, for example a carboxylic acid ester, preferably an ester of a carboxylic acid having up to 7 carbon atoms (for example, acetyl or benzoyl), an alkylsulfonic or arylsulfonic acid ester (wherein alkyl preferably contains 1 to 6 carbon atoms and aryl preferably containing 6 to 10 carbon atoms), or in the form of an ether, for example an alkyl ether (wherein alkyl preferably contains up to 6 carbon atoms), an aryl ether (wherein aryl preferably contains 6 to 10 carbon atoms) or an aralkyl ether (wherein the aralkyl preferably contains 7 to 11 carbon atoms). Boric acid esters, which are formed as intermediates in an oxidative hydroboronation, can also be used.

Compounds of Formula II wherein Q is —C(CH$_3$) (OZnHal)—CH$_2$—COOA are preferably obtained by reacting a ketone of the formula Z—CO—CH$_3$ with an organo-zinc compound of the formula HalZn—CH$_2$COOA under the conditions of the Reformatsky reaction (see, for example, Organic Reactions, Vol. 1, page 1 et. seq.). The ketones can be obtained, for example, by a Friedel-Crafts acetylation of compounds of the formula Z—H on which they are based. The organo-zinc compounds are preferably prepared in situ from the corresponding halogenoacetic acid derivatives and zinc. Bromoacetic acid esters, particularly bromoacetic acid methyl and ethyl esters, are preferred as the halogenoacetic acid derivatives. The zinc can be employed in any desired form, for example as zinc dust, zinc foil or zinc wool or in granulated form. The reaction can be carried out in the absence or, preferably, in the presence, of a solvent. Examples of suitable solvents are hydrocarbons, such as benzene or toluene, and ethers, such as diethyl ether, THF or dioxane, and mixtures thereof. The addition of iodine or trimethyl borate can be advantageous. Suitable reaction temperatures are from 0° to 150° C., preferably from 20° C. to the boiling point of the reaction mixture. The resulting zinc complex can be hydrolyzed to give an alkyl ester of Formula I (Y = COOA). Under more vigorous conditions of hydrolysis, the ester is saponified in the reaction mixture to give the corresponding acid of Formula I (Y = COOH).

A corresponding organolithium compound or Grignard compound of the formula M—CH$_2$—Y (M = Li or MgHal) can also be reacted with a ketone of the formula Z—CO—CH$_3$ under identical or similar conditions, a metal alcoholate of Formula II (Q = —C(CH$_3$) (OM)—CH$_2$—Y being formed. A variant of this synthesis consists of reacting a ketone Z—CO—CH$_3$ with acetic acid in the presence of an alkali metal, preferably Li or Na, and an aromatic hydrocarbon, preferably naphthalene or phenanthrene. In the course of this reaction, the dianion of a compound of the formula MCH$_2$COOM (M = alkali metal) is formed as an intermediate.

Metal alcoholates of the formula Z—C(CH$_3$) (OM)—CH$_2$—Y (M = Li or MgHal) can also be obtained by reacting a ketone of the formula Z—CO—CH$_2$—Y with an organo-metal compound of the formula CH$_3$M (M = Li or MgHal), such as methyl-lithium, methylmagnesium bromide or methylmagnesium iodide, or by reacting a ketone of the formula CH$_3$COCH$_2$Y with an organo-metal compound of the formula Z—M (M = Li or MgHal), such as 4-biphenylylmagnesium bromide, 4-phenoxyphenyllithium or 4-p-fluorophenoxyphenyllithium. Ketones of the formula Z—CO—CH$_2$—Y can be obtained by a Friedel-Crafts acylation of a compound of the formula Z—H using an acid halide of the formula Cl—CO—CH$_2$Y; keto-esters of the formula Z—CO—CH$_2$—COOA can be obtained, for example, using malonic ester chlorides. The corresponding keto-acids can be obtained by subsequent saponification. The Grignard reactions and the reactions with organolithium compounds referred to above are preferably carried out under the same or similar conditions as those indicated above for the Reformatsky reaction.

The metal alcoholates of Formula II (Q = —C(CH$_3$) (OM)—CH$_2$—Y, M = Li, MgHal or ZnHal), are preferably not isolated, but, after their formation, are hydrolyzed in situ using a fairly dilute acid, for example sulfuric acid or hydrochloric acid, or aqueous ammonium chloride solution, compounds of Formula I being obtained.

Compounds of Formula I can also be prepared by solvolysis of an acid derivative of the formula Z—C(CH$_3$) (OH)—CH$_2$—W. In these compounds, W is preferably one of the following radicals (wherein the R' and R" groups which are to be split off can be radicals of any desired kind and are, for example, alkyl having preferably 1 to 4 carbon atoms, the alkyl groups being the same or different or together form, for example, tetramethylene or pentamethylene, optionally interrupted by O): CHal$_3$; COOR''' (wherein R''' is a radical different from A, particularly alkyl having 7 to 12 carbon atoms or an alkyl radical different from A substituted in any desired way); C(OR')$_3$; COOAcyl (wherein Acyl is the radical of a carboxylic acid having up to 20 carbon atoms, preferably an acyl radical of the formula Z—C(CH$_3$) (OH)—CH$_2$—CO—); CN; CONH$_2$; CONHR'; CONR'R"; CONHOH; C(OH)=NOH; CONHNH$_2$; CON$_3$; C(OR')=NH; C(NH$_2$)=NNH$_2$; C(NHNH$_2$)=NH; CSOH; COSH; CSOR'; CSNH$_2$; CSNHR' or CSNR'R". W is preferably a nitrile group or an acid amide group.

Compounds of the formula Z—C(CH$_3$) (OH)—CH$_2$—W can be obtained in a known manner, and the hydroxy-esters Z—C(CH$_3$) (OH)—CH$_2$—COOR''' can be obtained, for example, by reacting a ketone of the formula Z—CO—CH$_3$ with an ester of the formula Hal—CH$_2$—COOR''' in the presence of zinc. Halogen derivatives of the formula Z—CHal(CH$_3$)—CH$_2$—Y can be prepared, for example, by an addition reaction between a hydrogen halide and a suitable unsaturated compound of the formula Z—C(CH$_3$)=CH—Y.

Compounds of Formula II wherein X is Cl, Br, I or an acylated OH group, or wherein W is CH$_2$Hal or CH$_2$OAcyl, are preferably saponified in an aqueous or aqueous alcoholic solution or suspension, with the addition, if desired, of a solubilizer, for example an alcohol, glycol or glycol ether. Alkalis, such as NaOH or KOH, alkaline earth metal hydroxides, such as Ca(OH)$_2$ or Ba(OH)$_2$, or also suspensions of Pb(OH)$_2$ or AgOH, are preferably used as the saponifying agent. Alcohols, such as methanol, ethanol or isopropanol, and mixtures thereof with water, are preferably used as the solvent. The saponification is preferably carried out at a temperature of from 20° to 100° C., preferably from 60° to 100° C.

Halogen atoms in compounds of Formula II wherein Q is —C(CH$_3$) (OH)—CH$_2$—CH$_2$Hal can also be converted into the corresponding acyloxy groups by treatment with a salt of a fatty acid, for example potassium acetate or heavy metal acetates, in an inert solvent, such as dimethylformamide, at a temperature of from 20° to 100° C.

Halogen atoms or ester groups which are linked to a tertiary carbon atom in compounds of Formula II wherein Q is —CHal(CH$_3$)—CH$_2$—Y or —C(OAcyl) (CH$_3$)—CH$_2$—Y can also be replaced by OH or can be removed by the action of water, preferably in the presence of a catalytically active amount of a mineral acid, e.g., sulfuric acid, preferably at a temperature of from 20° to 100° C., more preferably 40° to 60° C.

Etherified OH groups are preferably hydrolyzed by the action of a hydrogen halide acid, such as HBr or HI, the reaction advantageously being carried out in acetic acid or aqueous acetic acid at a temperature of from 60° C. to the boiling point, particularly at the boiling point. The halogen compounds formed are generally hydrolyzed subsequently using alcoholic alkali as described above.

Nitriles of Formula II (W = CN) and amides of Formula II (W = CONH$_2$, CONHR' or CONR'R") are preferably hydrolyzed in an alkaline medium (for example, using aqueous alcoholic alkali).

Compounds of Formula I can also be obtained by reducing compounds which otherwise correspond to Formula I but which contain additionally or instead of one or more H atoms, at least one group which can be reduced or can be replaced by a hydrogen atom. Preferred starting materials for the reduction are compounds of Formula VII:

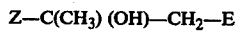   VII wherein E is a free or functionally modified —COOH or —CHO group or benzyloxymethyl, but is different from Y, and Z has the values given above.

More particularly, E is preferably COOR$^4$ (wherein R$^4$ is an alkyl group having more than 7, preferably 7 to 12, carbon atoms), CHO as well as COHal, CN, CONH$_2$, CON$_3$, COOAcyl (wherein Acyl has the values given above) or another ether group which can be split by hydrogenolysis, e.g., diphenylmethyloxymethyl or triphenylmethyloxymethyl. Compounds which have at least one substituent on a benzene ring which can be removed reductively (for example NH$_2$), are also suitable as starting materials for the reduction.

The alkyl esters mentioned can be obtained, for example, from ketones of the formula Z—CO—CH$_3$ by means of zinc and bromoacetic acid alkyl esters. They can be readily converted (for example by saponification, amidization or reduction) into the other abovementioned functional derivatives of the acids.

Catalytically activated hydrogen or complex metal hydrides are preferably used for the reduction. It is also possible to use other conventional reducing agents, for example metals conjointly with acids or bases.

Examples of suitable catalysts for catalytic hydrogenations are noble metal, nickel or cobalt catalysts and also mixed catalysts, such as copper-chromium oxide. Suitable noble metals are, in particular, platinum and palladium, which can be present on supports (for example charcoal, calcium carbonate or strontium carbonate), as oxides or in a finely divided form. Nickel and cobalt catalysts are preferably employed as Raney metals. The hydrogenation can be carried out at a pressure of from 1 to 100 atmospheres and at a temperature of from −80° to +150° C., preferably from 20° to 100° C. The hydrogenation is carried out in the presence of an inert solvent, for example an alcohol, such as methanol, ethanol or isopropanol; a carboxylic acid, such as acetic acid; an ester, such as ethyl acetate; or an ether, such as THF or dioxane. Mixtures of two or more solvents, for example mixtures containing water, can also be used.

Suitable complex metal hydrides for use as reducing agents include LiAlH$_4$, NaBH$_4$ and diborane, optionally with the addition of catalysts such as BF$_3$, AlCl$_3$ or LiBr. Suitable solvents in this case are, in particular, ethers, such as diethyl ether, THF, dioxane, 1,2-dimethoxyethane or diglyme. In the case of a reduction with NaBH$_4$, suitable solvents are, in particular, alcohols, such as methanol or ethanol. The reduction is preferably carried out at a temperature of from −80° to +150° C., more preferably from 20° to 120° C.

A further suitable method of reduction, for example for the aldehydes or esters mentioned, is reaction with nascent hydrogen. The latter can be generated, for example, by treating metals with acids or bases. Examples of systems which can be used are zinc/acid, zinc-/alkali metal hydroxide solution, iron/acid and tin/acid. Sodium, or another alkali metal, in an alcohol, such as ethanol, isopropanol, n-butanol, amyl alcohol or isoamyl alcohol or phenol; an aluminum/nickel alloy in an aqueous alkaline solution, if desired with added methanol; and sodium amalgam or aluminum amalgam in aqueous alcoholic solution or aqueous solution, can also be used to generate the nascent hydrogen. In this method, the reaction temperature is suitably from 0° to 150° C., preferably from 20° to 120° C.

Amino groups present on the aromatic rings can be removed by reduction, by first diazotizing the amino groups and then reducing the resulting diazonium salts in situ, for example by boiling with ethanol, formic acid, $H_3PO_2$ or stannite solutions.

The compounds of Formula I can also be obtained by oxidation of compounds of Formula III, for example, with $CrO_3$ or $KMnO_4$ or with air or oxygen in the presence of a catalyst such as $CuO/CaCO_3$ or $Ca(OH)_2$. The compounds of Formula III can in turn be prepared, for example, by condensation of ketones of the formula Z—CO—CH$_3$ with malonic acid, subsequent decarboxylation and hydrogenation and, if desired, esterification and/or reduction of the ester group.

The compounds of Formula I can also be obtained by reacting a compound of Formula IV or a salt thereof with a compound of Formula V or a salt thereof. The starting materials of Formula IV can be obtained, for example, by reaction of a p-$Q^1$-acetophenone with a bromoacetic acid alkyl ester and zinc, if desired, followed by saponification and/or reduction. The starting materials of Formula V are, for the most part, known.

A phenol of Formula IV ($Q_1$ = OH) can be reacted with a compound of Formula V ($Q^2$ = X) or a compound of Formula IV ($Q^1$ = X) can be reacted with a phenol of Formula V ($Q^2$ = OH). In this reaction, the phenol is preferably in the form of the corresponding phenolate, especially the sodium phenolate or potassium phenolate. The reaction is suitably carried out in the presence of an inert solvent, such as DMF or phosphoric acid hexamethyltriamide (HMPT), in the presence of a catalyst, such as copper powder, at a temperature of from 50° to 200° C., preferably from 80° to 130° C.

Compounds of Formula I which contain halogen can also be obtained from the corresponding amino compound of Formula VI by first diazotizing the latter, for example, with a salt or ester of nitrous acid (such as $NaNO_2$ or n-butyl nitrite) in aqueous hydrochloric acid at a temperature of from $-20°$ to $+10°$ C., and then converting the resulting diazonium salt into the halogen compound. Fluorine compounds (I, $R^1$ = F) are preferably obtained by reaction with $HBF_4$ to give the diazonium tetrafluoborate followed by thermal decomposition at from 100° to 200° C. in the absence of presence of an inert solvent, such as toluene, xylene or dioxane. Decomposition may also be effected at room temperature in an aqueous medium in the presence of copper powder. If the diazotization is carried out with $NaNO_2$ in anhydrous hydrofluoric acid, the desired fluorine compound is obtained directly on subsequent warming. Replacement of the diazonium group by chlorine or bromine is preferably carried out in hot aqueous solution in the presence of $Cu_2Cl_2$ or $Cu_2Br_2$. The starting materials of Formula VI can be obtained, for example, by reduction of corresponding 3-hydroxybutyric acid esters having a nitro group instead of the radical $R^1$.

The Y radical in a resulting compound of Formula I can, if desired, be converted into another Y radical by reduction, oxidation, solvolysis, esterification or transesterification, in accordance with methods described in the literature.

In particular, an acid or ester of Formula I (Y = $COOR^2$) may be reduced to the corresponding alcohol of Formula I (Y = $CH_2OH$), preferably with $LiAlH_4$ in accordance with the above-mentioned methods.

Conversely, an alcohol of Formula I (Y = $CH_2OH$) can be oxidized to the corresponding carboxylic acid of Formula I (Y = COOH) in accordance with known methods, for example with $KMnO_4$ or $CrO_3$.

The R group in a compound of Formula I can be converted into another R group by treatment with solvolyzing agents. In particular, an ester of Formula I (Y = COOA) can be saponified to a corresponding acid of Formula I (Y = COOH) or an ester of Formula I (Y = $CH_2OAlkanoyl$) can be saponified to the corresponding alcohol of Formula I (Y = $CH_2OH$). The solvolysis or saponification can be carried out in accordance with one of the above-mentioned methods for the solvolysis of the compounds of Formula II. The esters are preferably saponified by treatment with an alcoholic alkali solution, for example ethanolic potassium hydroxide, at a temperature of from 20° to 120° C., more preferably at the boiling temperature.

An acid of Formula I (Y = COOH) can be esterified with an alcohol of the formula A-OH, or a diol of Formula I (Y = $CH_2OH$) can be esterified with an alkanoic acid having up to 6 carbon atoms (or one of its reactive derivatives, for example, a halide or anhydride, such as acetyl chloride, acetyl bromide or acetic anhydride). The esterification is suitably carried out in the presence of an acidic or basic catalyst, for example an inorganic or organic acid, such as HCl, HBr, HI, $H_2SO_4$, $H_3PO_4$, trifluoroacetic acid, benzenesulfonic acid or p-toluenesulfonic acid, or an acidic ion exchanger, or of a base, for example of an alkali metal hydroxide, such as NaOH or KOH, an alkali metal carbonate, such as sodium carbonate or potassium carbonate, or an organic base, such as pyridine, if desired in the presence of an inert solvent, such as benzene, toluene or xylene, at a temperature of from 0° to 140° C., preferably from 20° to 100° C. In the esterification of the acid of Formula I (Y = COOH), the alcohol is preferably used in excess. The esterification of a diol of Formula I (Y = $CH_2OH$) is preferably carried out with the appropriate acid chloride or acid anhydride in pyridine at room temperature. Esters can also be obtained by an addition reaction between a carboxylic acid of Formula I (Y = COOH) with an olefin (for example, isobutylene) or by reaction of the carboxylic acid with a diazoalkane, for example diazomethane. Furthermore, esters can be prepared by reaction of a metal salt of an acid of Formula I (Y = COOH), preferably an alkali metal salt, lead salt or silver salt, with a halide of the formula A-X or with the corresponding chlorosulfites of the formula A-OSOCl, the resulting adducts subsequently being thermally decomposed. The esterification can also be carried out in several stages. The diols of Formula I (Y = $CH_2OH$) can also be esterified with ketenes. Formates of Formula I (Y = $CH_2O$—CHO) can suitably be obtained from the corresponding diol by heating with an excess of formic acid.

The desired esters of Formula I (Y = COOA) can also be obtained by trans-esterification, particularly by reaction of another ester with an excess of the appropriate alcohol or by reaction of a carboxylic acid of Formula I (Y = COOH) with any other ester of the appropriate alcohol (preferably alkanoates wherein the alkanoyl radical has up to 4 carbon atoms), preferably in the presence of a basic or acid catalyst, for example sodium ethylate or sulfuric acid, and at a temperature of from 0° C., to boiling temperature, the latter being more preferred.

A chlorine or bromine atom may be introduced into a compound of Formula I ($R^1$ = H) by halogenation in accordance with methods described in the literature, to obtain a compound of Formula I ($R^1$ = Cl or Br). Halogenation can, for example, be effected by direct reaction with elementary chlorine or bromine in an inert solvent, such as ether, tetrachloromethane or acetic acid, preferably in the presence of a catalyst, for example, iron filings, iodine or $AlCl_3$, and at a temperature of from −30° to 100° C.

The acids of Formula I (Y = COOH) can be converted into a physiologically acceptable metal or ammonium salt thereof by reaction with the appropriate base. Salts which can be used are, in particular, the sodium, potassium, magnesium, calcium and ammonium salts, and also substituted ammonium salts, such as, for example, the dimethylammonium, diethylammonium and diisopropylammonium, monoethanolammonium, diethanolammonium and triethanolammonium, cyclohexylammonium, dicyclohexylammonium and dibenzylethylenediammonium salts.

Conversely, an acid of Formula I (Y = COOH) can be liberated from a metal or ammonium salt thereof by treating the latter with a strong acid.

The compounds of Formula I contain a center of asymmetry and are thus usually obtained in racemic form. The racemates can be separated into their optical antipodes by any of the know mechanical or chemical methods as described in the literature. For example, an acid of Formula I (Y = COOH) can be separated by the use of an optically active base and a diol of Formula I (Y = $CH_2OH$) can be separated by the use of an optically active acid via the diastereoisomeric ester or by forming an acid ester (for example, the phthalate) and resolving the latter by the use of an optically active base.

The novel compounds of this invention of Formula I and, when Y is COOH, their physiologically acceptable salts with bases, possess valuable pharmacological properties and are well tolerated. In particular, these compounds possess anti-inflammatory activity, which can be demonstrated in rats, for example, in the adjuvans-arthritis test using the method of Newbould (Brit. J. Pharmacol., 21, (1963), pages 127–136). Some of these compounds also possess cholesterol level-reducing and triglyceride level-reducing activity, which can be demonstrated in the serum of rats by the method of Levine et al. (Automation in Analytical Chemistry, Technicon Symposium 1967, Mediad, New York, pages 25–28) or by the method of Noble and Campbell (Clin. Chem., 16 (1970), pages 166–170). The compounds also exhibit analgesic, anti-pyretic, enzyme-inducing or fibrinolytic activity or are effective in inhibiting the aggregation of thrombocytes as can be observed by methods which are current for this purpose. The spectrum of activity of individual compounds can be determined by standard pharmacological screening tests.

The foregoing compounds can, therefore, be used as medicaments in human and veterinary medicine and also as intermediates for the preparation of other medicaments. For example, the biphenylyl derivatives of Formula I (Z = 4-biphenylyl) can be converted by chlorination into other valuable anti-inflammatory agents.

The compounds of this invention can be used in human or veterinary medicine in admixture with solid, liquid and/or semi-liquid inert, physiologically acceptable carriers or excipients. Suitable carriers are organic or inorganic substances which are suitable for parenteral or enteral administration or topical application and which do not react with the novel compounds, for example water, vegetable oils, benzyl alcohol, polyethylene glycols, gelatin, lactose, starch, magnesium stearate, talc, petroleum jelly and cholesterol. Compositions in the form of tablets, dragees, capsules, syrups, elixirs or suppositories are suitable for enteral administration. Compositions in the form of solutions, preferably oily or aqueous solutions, suspensions, emulsions or implants are suitable for parenteral administration, and ointments, creams or powders are suitable for topical application. Such compositions may be sterilized and/or may contain adjuvants, such as lubricants, preservatives, stabilizers and/or wetting agents, emulsifiers, salts for regulating the osmotic pressure, buffer substances, colorants, flavoring materials and/or aromas. They may, if desired, also contain one or more other active compounds.

The compounds of Formula I and their salts are, in general, administered similarly to known anti-inflammatory agents, such as Indomethacin, for the same general purposes. The daily dosage is preferably from 0.2 to 20 mg/kg. of body weight. Oral administration is preferred. When the composition is formulated in dosage unit form, each dosage unit preferably contains from 10 to 1000 mg., more preferably from 30 to 300 mg., of the active compound(s).

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, all temperatures are in ° C. The expression "standard working up" means: water and/or an organic solvent, such as benzene, chloroform or dichloromethane, is added, if necessary, to the reaction mixture, the resulting mixture is separated into two phases, the organic phase is dried over sodium sulfate, filtered and evaporated, and the product is purified by chromatography and/or crystallization.

EXAMPLE 1

(a) 21.2 g. of 4-phenoxyacetophenone and 11.1 ml. of bromoacetic acid ethyl ester are dissolved in a mixture of 75 ml. of benzene and 75 ml. of toluene. 40 ml. of this solution are added to 7 g. of zinc powder (previously washed successively with 1% hydrochloric acid, water and acetone, and then dried) and the mixture is heated to 70° while stirring and passing in nitrogen. After the reaction has begun, the remainder of the solution is added dropwise, the mixture is boiled for one hour and cooled and 40 ml. of 20% sulfuric acid are added dropwise in order to decompose the resulting alcoholate of the formula $C_6H_5O$—p—$C_6H_4$—$C(CH_3)$—(OZnBr)—$CH_2$—$COOC_2H_5$. The organic phase is separated off and standard working up gives 3-p-phenoxyphenyl-3-hydroxy-butyric acid ethyl ester.

The following are obtained similarly from the corresponding bromoacetic acid esters:

3-(4-Biphenylyl)-3-hydroxybutyric acid methyl ester,
3-(4-biphenylyl)-3-hydroxybutyric acid ethyl ester, m.p. 56°-57°,
3-(4-biphenylyl)-3-hydroxybutyric acid propyl ester,
3-(4-biphenylyl)-3-hydroxybutyric acid isopropyl ester,
3-(4-biphenylyl)-3-hydroxybutyric acid n-butyl ester,
3-(4-biphenylyl)-3-hydroxybutyric acid isobutyl ester,
3-(4-biphenylyl)-3-hydroxybutyric acid sec.-butyl ester,
3-(4-biphenylyl)-3-hydroxybutyric acid tert.-butyl ester,
3-p-phenoxyphenyl-3-hydroxybutyric acid methyl ester,
3-p-phenoxyphenyl-3-hydroxybutyric acid propyl ester,
3-p-phenoxyphenyl-3-hydroxybutyric acid isopropyl ester,
3-p-phenoxyphenyl-3-hydroxybutyric acid n-butyl ester,
3-p-phenoxyphenyl-3-hydroxybutyric acid isobutyl ester,
3-p-phenoxyphenyl-3-hydroxybutyric acid sec.-butyl ester, and
3-p-phenoxyphenyl-3-hydroxybutyric acid tert.-butyl ester.

(b) 10 g. of 3-p-phenoxyphenyl-3-hydroxybutyric acid ethyl ester are dissolved in 50 ml. of ethanol and the solution is boiled for 15 minutes with 2 g. of KOH, evaporated and subjected to standard working up to give 3-p-phenoxyphenyl-3-hydroxybutyric acid, m.p. 137°-138°. Cyclohexylamine salt, m.p. 188°-189°.

3-(4-Biphenylyl)-3-hydroxybutyric acid, m.p. 137°-138°, is obtained analogously from the corresponding ethyl ester.

(c) 3 g. of 3-p-phenoxyphenyl-3-hydroxybutyric acid ethyl ester are dissolved in 20 ml. of acetic acid and a solution of 0.8 g. of chlorine in 20 ml. of acetic acid is added dropwise with stirring at 20° and the mixture is stirred for a further hour, evaporated and subjected to standard working up to give 3-p-(p-chlorophenoxy)-phenyl-3-hydroxybutyric acid ethyl ester, $n_D^{20}$ 1.5456.

EXAMPLE 2

(a) A mixture of 20 g. of bromoacetic acid ethyl ester, 23.1 g. of p-(p-fluorophenoxy)-acetophenone and 8 g. of zinc foil is added to 100 ml. of benzene and the mixture is boiled with stirring for one hour. After cooling, dilute sulfuric acid is added in order to decompose the resulting alcoholate and standard working up is effected to give 3-p-(p-fluorophenoxy)-3-hydroxybutyric acid ethyl ester.

The following are obtained analogously from the corresponding bromoacetic acid esters:

3-p-(p-Fluorophenoxy)-phenyl-3-hydroxybutyric acid methyl ester,
3-p-(p-fluorophenoxy)-phenyl-3-hydroxybutyric acid propyl ester,
3-p-(p-fluorophenoxy)-phenyl-3-hydroxybutyric acid isopropyl ester,
3-p-(p-fluorophenoxy)-phenyl-3-hydroxybutyric acid n-butyl ester,
3-p-(p-fluorophenoxy)-phenyl-3-hydroxybutyric acid isobutyl ester,
3-p-(p-fluorophenoxy)-phenyl-3-hydroxybutyric acid sec.-butyl ester, and
3-p-(p-fluorophenoxy)-phenyl-3-hydroxybutyric acid tert.-butyl ester.

(b) 1 g. of 3-p-(p-fluorophenoxy)-phenyl-3-hydroxybutyric acid ethyl ester is allowed to stand for 24 hours with 0.2 g. of NaOH in 40 ml. of isopropanol, and standard working up of the mixture gives 3-p-(p-fluorophenoxy)-phenyl-3-hydroxybutyric acid. Cyclohexylamine salt, decomposition at 190°.

EXAMPLE 3

(a) 2.46 g. of 4-p-chlorophenoxyacetophenone and 1.5 g. of bromoacetic acid ethyl ester are added to a mixture of 6.5 g. of granulated zinc (previously washed with dilute hydrochloric acid, water and acetone, and then dried) and 0.2 g. of iodine in 70 ml. of benzene and 70 ml. of diethyl ether. The mixture is boiled for 4 hours with occasional shaking, 5 g. of zinc and a trace of iodine being added after 1, 2 and 3 hours, and a further 1.5 g. of bromoacetic acid ethyl ester being added after 2 hours. After cooling, acetic acid and ethanol are added in order to decompose the resulting alcoholate to give a solution which is poured into water, and standard working up gives 3-p-(p-chlorophenoxy)-phenyl-3-hydroxybutyric acid ethyl ester; $n_D^{20}$ 1.5456.

The following are obtained analogously, using the corresponding bromoacetic acid esters:

3-p-(p-Chlorophenoxy)-phenyl-3-hydroxybutyric acid methyl ester,
3-p-(p-chlorophenoxy)-phenyl-3-hydroxybutyric acid propyl ester,
3-p-(p-chlorophenoxy)-phenyl-3-hydroxybutyric acid isopropyl ester,
3-p-(p-chlorophenoxy)-phenyl-3-hydroxybutyric acid n-butyl ester,
3-p-(p-chlorophenoxy)-phenyl-3-hydroxybutyric acid isobutyl ester,
3-p-(p-chlorophenoxy)-phenyl-3-hydroxybutyric acid sec.-butyl ester,
3-p-(p-chlorophenoxy)-phenyl-3-hydroxybutyric acid tert.-butyl ester, and
3-p-(p-chlorophenoxy)-phenyl-3-hydroxybutyric acid n-hexyl ester.

(b) 1 g. of 3-p-(p-chlorophenoxy)-phenyl-3-hydroxybutyric acid ethyl ester is boiled for one hour with 0.5 g. of potassium carbonate in 25 ml. of methanol, and the mixture is subjected to standard working up to give 3-p-(p-chlorophenoxy)-phenyl-3-hydroxybutyric acid; cyclohexylamine salt, m.p. 183°-184°.

EXAMPLE 4

(a) The following are obtained by the procedure described in Example 1, using p-(o-fluorophenoxy)-acetophenone, p-(m-fluorophenoxy)-acetophenone, p-(o-chlorophenoxy)-acetophenone, p-(m-chlorophenoxy)-acetophenone, p-(o-bromophenoxy)-acetophenone, p-(m-bromophenoxy)-acetophenone or p-(p-bromophenoxy)-acetophenone, as the starting material:

3-p-(o-Fluorophenoxy)-phenyl-3-hydroxybutyric acid methyl ester,
3-p-(o-fluorophenoxy)-phenyl-3-hydroxybutyric acid ethyl ester,
3-p-(m-fluorophenoxy)-phenyl-3-hydroxybutyric acid methyl ester,
3-p-(m-fluorophenoxy)-phenyl-3-hydroxybutyric acid ethyl ester,
3-p-(o-chlorophenoxy)-phenyl-3-hydroxybutyric acid methyl ester,
3-p-(o-chlorophenoxy)-phenyl-3-hydroxybutyric acid ethyl ester, 3-p-(m-chlorophenoxy)-phenyl-3-hydroxybutyric acid methyl ester,
3-p-(m-chlorophenoxy)-phenyl-3-hydroxybutyric acid ethyl ester,
3-p-(o-bromophenoxy)-phenyl-3-hydroxybutyric acid methyl ester,
3-p-(o-bromophenoxy)-phenyl-3-hydroxybutyric acid ethyl ester,
3-p-(m-bromophenoxy)-phenyl-3-hydroxybutyric acid methyl ester,
3-p-(m-bromophenoxy)-phenyl-3-hydroxybutyric acid ethyl ester,
3-p-(p-bromophenoxy)-phenyl-3-hydroxybutyric acid methyl ester, and
3-p-(p-bromophenoxy-phenyl-3-hydroxybutyric acid ethyl ester.

(b) The following acids are obtained in the same way as in Example 1b), by alkaline saponification of the previously mentioned esters:
3-p-(p-Fluorophenoxy)-phenyl-3-hydroxybutyric acid,
3-p-(m-fluorophenoxy)-phenyl-3-hydroxybutyric acid,
3-p-(o-chlorophenoxy)-phenyl-3-hydroxybutyric acid,
3-p-(m-chlorophenoxy)-phenyl-3-hydroxybutyric acid,
3-p-(o-bromophenoxy)-phenyl-3-hydroxybutyric acid,
3-p-(m-bromophenoxy)-phenyl-3-hydroxybutyric acid, and
3-p-(p-bromophenoxy)-phenyl-3-hydroxybutyric acid, m.p. 108°–109°.

EXAMPLE 5

(a) 25.6 g. of naphthalene, 4.6 g. of finely divided sodium and 150 ml. of THF are well mixed under nitrogen and cooled to −15°. A solution of 6 g. of acetic acid in 10 ml. of THF is added dropwise, the mixture is heated at 50° for 2 hours, a solution of 23.1 g. of p-(p-fluorophenoxy)-acetophenone in 100 ml. of ether is added and the whole is stirred for two hours.

Water is added in order to decompose the resulting alcoholate and the mixture is subjected to standard working up to give 3-p-(p-fluorophenoxy)-phenyl-3-hydroxybutyric acid.

(b) An ethereal diazomethane solution is added at 20° to a solution of 1 g. of 3-p-(p-fluorophenoxy)-phenyl-3-hydroxybutyric acid in 20 ml. of ether until there is a permanent yellow coloration. After evaporation, 3-p-(p-fluorophenoxy)-phenyl-3-hydroxybutyric acid methyl ester is obtained.

(c) 1 g. of 3-p-(p-fluorophenoxy)-phenyl-3-hydroxybutyric acid is allowed to stand for 24 hours at 20° with 20 ml. of ethanolic hydrochloric acid and the mixture is evaporated to give 3-p-(p-fluorophenoxy)-phenyl-3-hydroxybutyric acid ethyl ester.

EXAMPLE 6

A Grignard solution obtained from 14.2 g. of methyl iodide and 2.4 g. of magnesium in 100 ml. of THF is added dropwise to a solution of 28.4 g. of 4-phenoxybenzoyl-acetic acid ethyl ester in 200 ml. of THF. After the completion of the addition, the mixture is heated with stirring on a water bath for a further 2 hours and colled and the resulting alcoholate is hydrolyzed by means of ice and saturated NH$_4$Cl solution. The ethereal phase is dried and evaporated to give 3-p-phenoxyphenyl-3-hydroxybutyric acid ethyl ether.

EXAMPLE 7

A solution of p-phenoxyphenylmagnesium bromide (obtained from 2.49 g. of 4-bromodiphenyl ether and 0.24 g. of magnesium in 100 ml. of ether) is added dropwise at 20°, with stirring, to a solution of 1.3 g. of acetoacetic acid ethyl ester in 40 ml. of ether, and the mixture is stirred for a further two hours, the resulting alcoholate is decomposed by means of ice and saturated NH$_4$Cl solution, and the ethereal phase is dried and evaporated to give 3-p-phenoxyphenyl-3-hydroxybutyric acid ethyl ester.

EXAMPLE 8

A solution of 2.26 of 1-p-biphenylyl-3-hydroxypropan-1-one (obtainable by acylating biphenyl with 3-methoxypropionyl chloride to give 1-p-biphenylyl-3-methoxypropan-1-one and subsequent ether splitting) in 20 ml. of THF is added dropwise at 20°, with stirring, to a Grignard solution prepared from 3 g. of methyl iodide and 0.5 g. of magnesium in 100 ml. of ether. The mixture is stirred for a further 4 hours, the resulting alcoholate is decomposed by means of water and dilute sulfuric acid, and standard working up gives 3-p-biphenylyl-1,3-butanediol, m.p. 115°–117°.

EXAMPLE 9

0.44 g. of 1-hydroxy-3-butanone in 40 ml. of ether is added dropwise at 20°, with stirring, to a Grignard solution prepared from 2.33 g. of 4-bromobiphenyl and 0.24 g. of magnesium in 100 ml. of ether. The mixture is stirred for a further two hours, the resulting alcoholate is decomposed by means of dilute sulfuric acid, and standard working up gives 3-p-biphenylyl-1,3-butanediol, m.p. 115°–117°.

EXAMPLE 10

2.24 g. of 3-p-biphenylyl-1-buten-3-ol (obtainable from p-biphenylylmagnesium bromide and methyl vinyl ketone) are dissolved in 5 ml. of diglyme, 3 ml. of a 1 M solution of NaBH$_4$ in diglyme are added and a solution of 0.56 g. of BF$_3$ etherate in 1.2 ml. of diglyme is added dropwise under N$_2$. 0.7 ml. of water is then added and 1.4 ml. of 3N NaOH and 1.4 ml. of 30% H$_2$O$_2$ are then added dropwise at 80°–100°. The mixture is cooled, treated with ice water, and standard working up gives 3-p-biphenylyl-1,3-butanediol, m.p. 115°–117° (the boric acid ester formed as an intermediate being hydrolyzed).

EXAMPLE 11

1 g. of 3-p-phenoxyphenyl-3-hydroxybutyronitrile (obtainable from 1-bromo-2-p-phenoxyphenyl-2-propanol and KCN) is boiled with 10 ml. of 25% sodium hydroxide solution for 10 hours under nitrogen. The mixture is washed with ether and acidified to give 3-p-phenoxyphenyl-3-hydroxybutyric acid, m.p. 137°–138°.

EXAMPLE 12

3. g. of 3-p-phenoxyphenyl-3-hydroxybutyric acid amide (obtainable from 4-phenoxyacetophenone and bromoacetamide/zinc) and 5 g. of KOH in 100 ml. of ethanol are boiled for 3 hours under nitrogen. The mixture is evaporated and worked up to give 3-p-phenoxyphenyl-3-hydroxybutyric acid, m.p. 137°–138°.

EXAMPLE 13

1 g. of 3-chloro-3-p-phenoxyphenyl-butyric acid (obtainable by an addition reaction of HCl with 3p-phenoxyphenyl-2-butenoic acid) and 25 ml. of 20% potassium hydroxide solution are boiled for 10 minutes, cooled, washed with ether and acidified to give 3-p-phenoxyphenyl-3-hydroxybutyric acid, m.p. 137°–138°.

EXAMPLE 14

3.55 g. of 3-bromo-3-p-(p-chlorophenoxy)-phenyl-1-butanol (obtainable by brominating 3-p-(p-chlorophenoxy)-phenyl-1-butanol) are dissolved in a mixture of 15 ml. of acetone and 15 ml. of water, 1 drop of sulfuric acid is added and the mixture is warmed at 45° for 4 hours, and standard working up gives 3-p-(p-chlorophenoxy)-phenyl-1,3-butanediol; $n_D^{20}$ 1.5838.

EXAMPLE 15

2.94 g. of 1-chloro-3-(4-p-fluorophenoxy-phenyl)-3-butanol (obtainable by reacting 4-(3-chloropropionyl)-4′-fluorodiphenyl ether with $CH_3MgI$ and subsequently hydrolyzing) are boiled for 3 hours with a solution of 2 g. of $Ba(OH)_2$ in 40 ml. of methanol, water is added and the mixture is extracted with chloroform, and the extract is evaporated to give 3-p-(p-fluorophenoxy)-phenyl-1,3-butanediol; $n_D^{20}$ 1.5583.

EXAMPLE 16

(a) 2.6 g. of 1-chloro-3-p-biphenylyl-3-butanol (obtainable from p-biphenylylmagnesium bromide and 1-chloro-3-buranone) are dissolved in 20 ml. of DMF, 3 g. of anhydrous potassium acetate are added and the mixture is stirred for 3 hours at 60°. After standard working up, 1-acetoxy-3-p-biphenylyl-3-butanol is obtained.

(b) A solution of 2.84 g. of 1-acetoxy-3-p-biphenylyl-3-butanol and 2 g. of NaOH in 30 ml. of 80% ethanol is boiled for 3 hours. Water is added and the mixture is extracted with chloroform and the extract is evaporated to give 3-p-biphenylyl-1,3-butanediol, m.p. 115°–117°.

EXAMPLE 17

(a) 3-Bromo-3-p-biphenylyl-1-butanol (obtainable by brominating 3-p-biphenylyl-1-butanol) is reacted with potassium acetate, analogously to Example 16a), to give 3-acetoxy-3-p-biphenylyl-1-butanol.

(b) 2.84 g. of 3-acetoxy-3-p-biphenylyl-1-butanol are boiled for 2 hours with 2 g. of KOH in 50 ml. of methanol, water and chloroform are added and the mixture is worked up to give 3-p-biphenylyl-1,3-butanediol, m.p. 115°–117°.

EXAMPLE 18

A solution of 2.41 g. of 1-amino-3-p-biphenylyl-3-butanol (obtainable from 3-hydroxy-3-p-biphenylylbutyramide by means of $LiAlH_4$) in 50 ml. of 15% aqueous acetic acid is treated, while being cooled with ice, with a solution of 1 g. of $NaNO_2$ in 5 ml. of water. The mixture is heated at 80° for one hour and standard working up then gives 3-p-biphenylyl-1,3-butanediol, m.p. 115°–117°.

EXAMPLE 19

2.56 g. of 1-methoxy-3-p-biphenylyl-3-butanol (obtainable from 3-methoxy-1-p-biphenylyl-1-propanone and $CH_3MgI$) is boiled for 2 hours with a mixture of 5 ml. of 48% aqueous HBr and 5 ml. of acetic acid, 10 ml. of 10% methanolic KOH are added and boiling is continued for a further 2 hours and the mixture is worked up using water and chloroform to give 3-p-biphenylyl-1,3-butanediol m.p. 115°–117°.

EXAMPLE 20

A solution of 2.4 g. of 3-hydroxy-3-p-biphenylylbutanal (obtainable by reacting p-phenylacetophenone with 2,2-diethoxyethylmagnesium bromide and subsequently hydrolyzing) in 12 ml. of ethanol is added dropwise to a solution of 0.6 g. of $NaBH_4$ in 15 ml. of ethanol. The mixture is stirred for two hours at 20° and standard working up then gives 3-p-biphenylyl-1,3-butanediol, m.p. 115°–117°.

EXAMPLE 21

2 g. of 1-benzyloxy-3-p-(p-fluorophenoxy)-phenyl-3-butanol (obtainable from 4-p-fluorophenoxyphenylacetophenone and 2-benzyloxyethylmagnesium bromide) are dissolved in 50 ml. of methanol and are hydrogenated at 20° and normal pressure in the presence of 0.5 g. of 5% Pd-C catalyst until the absorption of hydrogen ceases, to give 3-p-(p-fluorophenoxy)-phenyl-1,3-butanediol; $n_D^{20}$ 1.5583.

EXAMPLE 22

2.89 g. of 3-(3-amino-4-phenoxyphenyl)-1,3-butanediol (obtainable by nitrating 3-p-chlorophenyl-1,3-butanediol to give 3-(3-nitro-4-chlorophenyl)-1,3-butanediol, reacting with phenol to give 3-(3-nitro-4-phenoxyphenyl)-1,3-butanediol and reducing the product with Sn/HCl) are mixed, with stirring, with 25 ml. of 15% hydrochloric acid, 0.69 g. of $NaNO_2$ in 2 ml. of water are added at 0°–5°, 30 ml. of ethanol are then added, and the mixture is then stirred for 30 minutes at 20° and is boiled for 30 minutes. After cooling, standard working up gives 3-p-phenoxyphenyl-1,3-butanediol, m.p. 74°–75°.

EXAMPLE 23

A stream of air is passed through a solution of 2.6 g. of 3-p-(p-fluorophenoxy)-phenyl-1-butanol (obtainable by reducing 3-p-(p-fluorophenoxy)-phenylbutyric acid ethyl ester) in 50 ml. of boiling toluene, in the presence of 1 g. of a $CuO/CaCO_3$ catalyst, for 8 hours. Standard working up then gives 3-p-(p-fluorophenoxy)-phenyl-1,3-butanediol, $n_D^{20}$ 1.5583.

EXAMPLE 24

A mixture of 2.22 g. of p-iodofluorobenzene and 2.4 g. of the disodium salt of 3-p-hydroxyphenyl-3-hydroxybutyric acid (obtainable by reacting p-hydroxyacetophenone with bromoacetic acid ethyl ester and zinc and subsequently saponifying) is heated at 90° for 8 hours in the presence of 1 g. of Cu powder in 10 ml. of HMPT. Standard working up then gives 3-p-(p-fluorophenoxy)-phenyl-3-hydroxybutyric acid, cyclohexylamine salt, decomposition at 190°.

3-p-(p-Fluorophenoxy)-phenyl-1,3-butanediol, $n_D^{20}$ 1,5583, is obtained analogously using the Na salt of 3-p-hydroxyphenyl-1,3-butanediol (obtainable by reducing 3-p-hydroxyphenyl-3-hydroxybutyric acid ethyl ester.

EXAMPLE 25

A solution of 3.28 g. of the sodium salt of 3-p-iodophenyl-3-hydroxybutyric acid and 1.34 g. of sodium p-fluorophenolate in 20 ml. of DMF is heated at 130° for 8 hours. Standard working up gives 3-p-(p-fluorophenoxy)-phenyl-3-hydroxybutyric acid, cyclohexylamine salt, decomposition at 190°.

3-p-Phenoxyphenyl-1,3-butanediol, m.p. 74°–75°, is obtained analogously from 3-p-iodophenyl-1,3-butanediol (obtainable by reducing 3-p-iodophenyl-3-hydroxybutyric acid ethyl ester) and sodium phenolate.

EXAMPLE 26

3 ml. of concentrated hydrochloric acid are added at 0° to 3.15 g. of 3-p-(p-aminophenoxy)-phenyl-3-hydroxybutyric acid ethyl ester (obtainable by a Reformatsky reaction from 4-p-acetamidophenoxyacetophenone, and a solution of 1.4 g. of NaNO$_2$ in 6 ml. of water is then added at 0°, with stirring. After adding a solution of 0.7 g. of boric acid in 1.5 g. of 60% hydrofluoric acid, the mixture is stirred for 40 minutes and the product is filtered off, washed with water, methanol and ether, and then dried. The diazonium salt is heated to about 150° until decomposition is complete. This gives 3-p-(p-fluorophenoxy)-phenyl-3-hydroxybutyric acid ethyl ester.

3-p-(p-Fluorophenoxy)-phenyl-1,3-butanediol, $n_D^{20}$ 1.5583, is obtained analogously from 3-p-(p-aminophenoxy)-phenyl-1,3-butanediol (obtainable by hydrogenating 3-p-(p-nitrophenoxy)-phenyl-3-hydroxybutyric acid ethyl ester over CuCr$_2$O$_4$).

EXAMPLE 27

3.15 g. of 3-p-(p-aminophenoxy)-phenyl-3-hydroxybutyric acid ethyl ester are dissolved in 30 ml. of 10% hydrochloric acid, 0.7 g. of NaNO$_2$ in 2 ml. of water are added at 0° to 5° and the resulting diazonium salt solution is added dropwise slowly to a hot solution of Cu$_2$Cl$_2$ (obtained by reducing 2.1 g. of copper sulfate with SO$_2$ in 13 ml. of water in the presence of 2.6 g. of NaCl), and the mixture is heated for a further 30 minutes at 90° to 95°, cooled and standard working up then gives 3-p-(p-chlorophenoxy)-phenyl-3-hydroxybutyric acid ethyl ester; $n_D^{20}$ 1.5456.

3-p-(p-Bromophenoxy)-phenyl-3-hydroxybutyric acid ethyl ester is obtained analogously, using Cu$_2$Br$_2$ and 3-p-(p-chlorophenoxy)-phenyl-1,3-butanediol, $n_D^{20}$ 1.5838, is obtained analogously from 3-p-(p-aminophenoxy)-phenyl-1,3-butanediol, using Cu$_2$Cl$_2$.

EXAMPLE 28

(a) A solution of 33.4 g. of 3-p-(p-chlorophenoxy)-phenyl-3-hydroxybutyric acid ethyl ester in 300 ml. of THF is added dropwise to a solution of 4.6 g. of LiAlH$_4$ in 100 ml. of THF, while stirring and passing N$_2$ through the mixture. The mixture is boiled for an hour and cooled and a mixture of 20 ml. of THF and 5 ml. of water is first added dropwise and 5 ml. of 32% sodium hydroxide solution are then added dropwise and the mixture is worked up with chloroform and water to give 3-p-(p-chlorophenoxy)-phenyl-1,3-butanediol, an oil, $n_D^{20}$ 1.5838.

3-p-Biphenylyl-1,3-butanediol, m.p. 115°–117°; 3-p-phenoxyphenyl-1,3-butanediol, m.p. 74°–75°; 3-p-(p-fluorophenoxy)-phenyl-1,3-butanediol, $n_D^{20}$ 1.5583; and 3-p-(p-bromophenoxy)-phenyl-1,3-butanediol are obtained analogously, by reduction with LiAlH$_4$, from 3-p-biphenylyl-3-hydroxybutyric acid ethyl ester, 3-p-phenoxyphenyl-3-hydroxybutyric acid ethyl ester, 3-p-(p-flourophenoxy)-phenyl-3-hydroxybutyric acid ethyl ester, and 3-p-(p-bromophenoxy)-phenyl-3-hydroxybutyric acid ethyl ester.

(b) A mixture of 2.92 g. of 3-p-(p-chlorophenoxy)-phenyl-1,3-butanediol, 5 ml. of acetic anhydride and 8 ml. of pyridine is allowed to stand at 20° for 15 hours and is poured into ice water and worked up using chloroform and water to give 1-acetoxy-3-p-(p-chlorophenoxy)-phenyl-3-butanol.

1-Acetoxy-3-p-phenoxyphenyl-3-butanol, 1-acetoxy-3-p-(p-fluorophenoxy)-phenyl-3-butanol, $n_D^{20}$ 1.5376, and 1-acetoxy-3-p-(p-bromophenoxy)-phenyl-3-butanol are obtained analogously by acetylating the corresponding diols.

(c) The corresponding propionates, butyrates, isobutyrates, valerates, isovalerates, trimethyl acetates, caproates, isocaproates and tert.-butyl acetates, for example:
1-propionyloxy-3-p-(p-chlorophenoxy)-phenyl-3-butanol,
1-butyryloxy-3-p-(p-chlorophenoxy)-phenyl-3-butanol,
1-isobutyryloxy-3-p-(p-chlorophenoxy)-phenyl-3-butanol,
1-valeryloxy-3-p-(p-chlorophenoxy)-phenyl-3-butanol,
1-isovaleryloxy-3-p-(p-chlorophenoxy)-phenyl-3-butanol,
1-trimethylacetoxy-3-p-(p-chlorophenoxy)-phenyl-3-butanol,
1-caproyloxy-3-p-(p-chlorophenoxy)-phenyl-3-butanol,
1-isocaproyloxy-3-p-(p-chlorophenoxy)-phenyl-3-butanol, and
1-tert.-butylacetoxy-3-p-(p-chlorophenoxy)-phenyl-3-butanol, are obtained, analogously to b), using the corresponding anhydrides.

(d) 2.92 g. of 3-p-(p-chlorophenoxy)-phenyl-1,3-butanediol are heated with 15 ml. of formic acid for 2 hours at 80° and the mixture is cooled and standard working up then gives 1-formyloxy-3-p-(p-chlorophenoxy)-phenyl-3-butanol.

1-Formyloxy-3-p-phenoxyphenyl-3-butanol, 1-formyloxy-3-p-(p-fluorophenoxy)-phenyl-3-butanol and 1-formyloxy-3-p-(p-bromophenoxy)-phenyl-3-butanol are obtained analogously from the corresponding diols.

(e) 2.58 g. of 3-p-phenoxyphenyl-1,3-butanediol are dissolved in 20 ml. of acetic acid, a solution of 0.8 g. of chlorine in 20 ml. of acetic acid is added dropwise with stirring at 20° and the mixture is stirred for a further hour and evaporated. Standard working up, using water and chloroform, gives 3-p-(p-chlorophenoxy)-phenyl-1,3-butanediol, $n_D^{20}$ 1.5838.

EXAMPLE 29

(a) 3-p-(p-Fluorophenoxy)-phenyl-3-hydroxybutyric acid is reduced, analogously to Example 28a, using LiAlH$_4$, but boiling for 8 hours. This gives 3-p-(p-fluorophenoxy)-phenyl-1,3-butanediol, an oil $n_D^{20}$ 1.5583.

The following are obtained analogously by reducing the corresponding acids or their esters:
3-p-(o-fluorophenoxy)-phenyl-1,3-butanediol,
3-p-(m-fluorophenoxy)-phenyl-1,3-butanediol,
3-p-(o-chlorophenoxy)-phenyl-1,3-butanediol,
3-p-(m-chlorophenoxy)-phenyl-1,3-butanediol,
3-p-(o-bromophenoxy)-phenyl-1,3-butanediol, and
3-p-(m-bromophenoxy)-phenyl-1,3-butanediol.

(b) The following are obtained, analogously to Example 28b, by acetylating the above-mentioned diols:
1-acetoxy-3-p-(o-fluorophenoxy)-phenyl-3-butanol,
1-acetoxy-3-p-(m-fluorophenoxy)-phenyl-3-butanol,
1-acetoxy-3-p-(o-chlorophenoxy)-phenyl-3-butanol,
1-acetoxy-3-p-(m-chlorophenoxy)-phenyl-3-butanol,
1-acetoxy-3-p-(o-bromophenoxy)-phenyl-3-butanol,
and
1-acetoxy-3-p-(m-bromophenoxy)-phenyl-3-butanol.

The following examples of pharmaceutical compositions containing active compounds of Formula I or physiologically acceptable salts thereof, are given by way of illustration.

EXAMPLE A: Tablets

A mixture consisting of 1 kg. of the cyclohexylamine salt of 3-p-(p-chlorophenoxy)-phenyl-3-hydroxybutyric acid, 4 kg. of lactose, 1.2 kg. of potato starch, 0.2 kg. of talc and 0.1 kg. of magnesium stearate is pressed into tablets in conventional manner so that each tablet contains 100 mg. of the active compound.

EXAMPLE B: Dragees

Tablets are pressed in the same way as in Example A, and are then coated in conventional manner with a coating consisting of sugar, maize starch, talc and tragacanth.

Tablets and dragees containing one or more of the other compounds of Formula I or their physiologically acceptable salts thereof are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

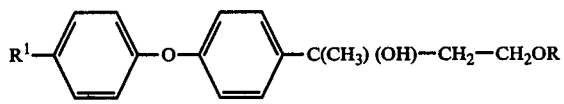

wherein R is H or alkanoyl of 1 to 6 carbon atoms and $R^1$ is F, Cl or Br.

2. A compound of claim 1, 3-p-(p-fluorophenoxy)-phenyl-1,3-butanediol.

3. A compound of claim 1, 3-p-(p-chlorophenoxy)-phenyl-1,3-butanediol.

4. A compound of claim 1, 3-p-(p-bromophenoxy)-phenyl-1,3-butanediol.

5. A compound of claim 1, 1-acetoxy-3-p-(p-fluorophenoxy)-phenyl-3-butanol.

6. A pharmaceutical composition comprising a compound of claim 1 in admixture with a physiologically acceptable carrier.

7. A method of treating inflammatory conditions which comprises administering to the affected patient an antiinflammatory effective amount of a compound of claim 1.

* * * * *